(12) United States Patent
Stark et al.

(10) Patent No.: US 10,702,644 B2
(45) Date of Patent: *Jul. 7, 2020

(54) TRANSCUTANEOUS POWER TRANSMISSION UTILIZING NON-PLANAR RESONATORS

(71) Applicant: TC1 LLC, St. Paul, MN (US)

(72) Inventors: Joseph Stark, Oakland, CA (US); Edward Burke, Waltham, MA (US)

(73) Assignee: TCI LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/375,573

(22) Filed: Apr. 4, 2019

(65) Prior Publication Data

US 2019/0231955 A1    Aug. 1, 2019

Related U.S. Application Data

(63) Continuation of application No. 14/796,983, filed on Jul. 10, 2015, now Pat. No. 10,279,096, which is a
(Continued)

(51) Int. Cl.
*A61M 1/12* (2006.01)
*H02J 50/12* (2016.01)
(Continued)

(52) U.S. Cl.
CPC ........... *A61M 1/127* (2013.01); *A61N 1/3787* (2013.01); *A61N 1/37229* (2013.01); *H01Q 1/36* (2013.01);
(Continued)

(58) Field of Classification Search
CPC ........ A61M 1/12; A61M 1/122; A61M 1/127; A61N 1/00; A61N 1/3787; A61N 1/37229;
(Continued)

(56) References Cited

U.S. PATENT DOCUMENTS 4,740,751 A    4/1988   Misic et al.
5,217,011 A *  6/1993   Bisch ................. A61N 1/37223
                                                 340/870.31
(Continued)

FOREIGN PATENT DOCUMENTS

GB    2 221 504 B     6/1992
JP    2003-348774 A   12/2003
JP    2010-119684 A   6/2010

OTHER PUBLICATIONS

Schuder, J.C. et al. "Energy Transport into the Closed Chest from a Set of Very-Large Mutually Orthogonal Coils," Communications and Electronics, 82(64):527-534, Jan. 1963.
(Continued)

*Primary Examiner* — Rexford N Barnie
*Assistant Examiner* — Jagdeep S Dhillon
(74) *Attorney, Agent, or Firm* — Womble Bond Dickinson (US) LLP

(57) ABSTRACT

A system for omni-orientational wireless energy transfer is described. A transmitter unit has a transmitter resonator with a coil that is configured to be coupled to a power supply to wirelessly transmit power to a receiver unit. A receiver unit has a receiver resonator with a coil coupled to a device load. At least one of the resonators is a non-planar resonator that spans a non-degenerate two-dimensional surface having at least one concave portion.

20 Claims, 6 Drawing Sheets

Related U.S. Application Data continuation of application No. 13/301,717, filed on Nov. 21, 2011, now Pat. No. 9,079,043.

(51) Int. Cl.
| | |
|---|---|
| *H02J 50/80* | (2016.01) |
| *A61N 1/372* | (2006.01) |
| *H02J 5/00* | (2016.01) |
| *H02J 7/02* | (2016.01) |
| *H04B 5/00* | (2006.01) |
| *H01Q 1/36* | (2006.01) |
| *H01Q 1/38* | (2006.01) |
| *A61N 1/378* | (2006.01) |
| *A61M 1/10* | (2006.01) |

(52) U.S. Cl.
CPC .............. *H01Q 1/38* (2013.01); *H02J 5/005* (2013.01); *H02J 7/025* (2013.01); *H02J 50/12* (2016.02); *H02J 50/80* (2016.02); *H04B 5/0037* (2013.01); *H04B 5/0093* (2013.01); *A61M 1/101* (2013.01); *A61M 1/12* (2013.01); *A61M 1/122* (2014.02); *A61M 2205/3515* (2013.01); *A61M 2205/3523* (2013.01); *A61M 2205/8243* (2013.01)

(58) Field of Classification Search
CPC ............ H02J 50/10; H02J 50/12; H02J 50/80; H01Q 1/36; H01Q 1/38
USPC .............................. 307/104, 149, 64, 66, 108
See application file for complete search history.

(56) References Cited

U.S. PATENT DOCUMENTS

| | | | |
|---|---|---|---|
| 5,350,413 A * | 9/1994 | Miller | A61N 1/3787 336/115 |
| 5,519,262 A | 5/1996 | Wood | |
| 6,212,430 B1 | 4/2001 | Kung | |
| 6,249,234 B1 * | 6/2001 | Ely | G01D 5/2073 178/18.06 |
| 6,327,504 B1 | 12/2001 | Dolgin et al. | |
| 6,563,425 B2 | 5/2003 | Nicholson et al. | |
| 6,772,011 B2 | 8/2004 | Dolgin | |
| 6,960,968 B2 | 11/2005 | Odenna et al. | |
| 7,239,110 B2 | 7/2007 | Cheng et al. | |
| 7,471,986 B2 | 12/2008 | Hatlested | |
| 7,639,514 B2 | 12/2009 | Baarman | |
| 7,741,734 B2 | 6/2010 | Joannopoulos et al. | |
| 7,825,543 B2 | 11/2010 | Karalis et al. | |
| 7,885,050 B2 | 2/2011 | Lee | |
| D636,333 S | 4/2011 | Kulikowski | |
| 8,035,255 B2 | 10/2011 | Kurs et al. | |
| 8,106,539 B2 | 1/2012 | Schatz et al. | |
| 8,204,605 B2 * | 6/2012 | Hastings | A61N 1/37229 607/119 |
| 8,304,935 B2 | 11/2012 | Karalis et al. | |
| 8,324,759 B2 | 12/2012 | Karalis et al. | |
| 8,400,017 B2 | 3/2013 | Kurs et al. | |
| 8,410,636 B2 | 4/2013 | Kurs et al. | |
| 8,441,154 B2 | 5/2013 | Karalis et al. | |
| 8,461,719 B2 | 6/2013 | Kesler et al. | |
| 8,461,720 B2 | 6/2013 | Kurs et al. | |
| 8,461,721 B2 | 6/2013 | Karalis et al. | |
| 8,461,722 B2 | 6/2013 | Kurs et al. | |
| 8,466,583 B2 | 6/2013 | Karalis et al. | |
| 8,471,410 B2 | 6/2013 | Karalis et al. | |
| 8,476,788 B2 | 7/2013 | Karalis et al. | |
| 8,482,158 B2 | 7/2013 | Kurs et al. | |
| 8,487,480 B1 | 7/2013 | Kesler et al. | |
| 8,497,601 B2 | 7/2013 | Hall et al. | |
| D692,010 S | 10/2013 | Verghese et al. | |
| 8,552,592 B2 | 10/2013 | Schatz et al. | |
| 8,569,914 B2 | 10/2013 | Karalis et al. | |
| 8,587,153 B2 | 11/2013 | Giler et al. | |
| 8,587,155 B2 | 11/2013 | Hall et al. | |
| 8,598,743 B2 | 12/2013 | Hall et al. | |
| 8,618,696 B2 | 12/2013 | Kurs et al. | |
| D697,477 S | 1/2014 | Jonas, III | |
| 8,629,578 B2 | 1/2014 | Kurs et al. | |
| 8,643,326 B2 | 2/2014 | Campanella et al. | |
| 8,667,452 B2 | 3/2014 | Verghese et al. | |
| 8,669,676 B2 | 3/2014 | Karalis et al. | |
| 9,079,043 B2 | 7/2015 | Stark et al. | |
| 10,279,096 B2 | 5/2019 | Stark et al. | |
| 2002/0087204 A1 * | 7/2002 | Kung | A61N 1/3787 607/61 |
| 2003/0133657 A1 * | 7/2003 | Kochergin | G01N 21/1717 385/37 |
| 2003/0195468 A1 | 10/2003 | Lal et al. | |
| 2005/0165461 A1 * | 7/2005 | Takeda | A61N 1/3787 607/61 |
| 2005/0187594 A1 | 8/2005 | Hatlested | |
| 2008/0067874 A1 | 3/2008 | Tseng | |
| 2008/0211320 A1 | 9/2008 | Cook et al. | |
| 2009/0045772 A1 | 2/2009 | Cook et al. | |
| 2009/0051224 A1 | 2/2009 | Cook et al. | |
| 2009/0072629 A1 | 3/2009 | Cook et al. | |
| 2009/0153273 A1 | 6/2009 | Chen et al. | |
| 2009/0195332 A1 | 8/2009 | Joannopoulos et al. | |
| 2009/0267709 A1 | 10/2009 | Joannopoulos et al. | |
| 2009/0267710 A1 | 10/2009 | Joannopoulos et al. | |
| 2009/0276016 A1 | 11/2009 | Phillips et al. | |
| 2009/0286470 A1 | 11/2009 | Mohammadian et al. | |
| 2010/0033021 A1 | 2/2010 | Bennett | |
| 2010/0036773 A1 | 2/2010 | Bennett | |
| 2010/0037902 A1 | 2/2010 | Wirtz et al. | |
| 2010/0102639 A1 | 4/2010 | Joannopoulos et al. | |
| 2010/0102641 A1 | 4/2010 | Joannopoulos et al. | |
| 2010/0109445 A1 | 5/2010 | Kurs et al. | |
| 2010/0117455 A1 | 5/2010 | Joannopoulos et al. | |
| 2010/0141042 A1 | 6/2010 | Kesler et al. | |
| 2010/0179614 A1 | 7/2010 | Kieval et al. | |
| 2010/0210233 A1 | 8/2010 | Cook et al. | |
| 2010/0219694 A1 | 9/2010 | Kurs et al. | |
| 2010/0231053 A1 | 9/2010 | Karalis et al. | |
| 2010/0237709 A1 | 9/2010 | Hall et al. | |
| 2010/0253152 A1 | 10/2010 | Karalis et al. | |
| 2010/0259108 A1 | 10/2010 | Giler et al. | |
| 2010/0308939 A1 * | 12/2010 | Kurs | H02J 5/005 333/219.2 |
| 2010/0331920 A1 * | 12/2010 | DiGiore | A61N 1/3787 607/61 |
| 2011/0040343 A1 | 2/2011 | Johnson et al. | |
| 2011/0160516 A1 | 6/2011 | Dague et al. | |
| 2011/0260925 A1 * | 10/2011 | Chirila | H01Q 1/38 343/700 MS |
| 2012/0001492 A9 * | 1/2012 | Cook | H01Q 7/00 307/104 |
| 2012/0046782 A1 | 2/2012 | Schultze et al. | |
| 2012/0139663 A1 | 6/2012 | Hsu | |
| 2012/0179011 A1 * | 7/2012 | Moon | A61B 5/7207 600/324 |
| 2012/0206096 A1 | 8/2012 | John et al. | |
| 2012/0313449 A1 | 12/2012 | Kurs et al. | |
| 2012/0313742 A1 | 12/2012 | Kurs et al. | |
| 2013/0007949 A1 | 1/2013 | Kurs et al. | |
| 2013/0020878 A1 | 1/2013 | Karalis et al. | |
| 2013/0033118 A1 | 2/2013 | Karalis et al. | |
| 2013/0038402 A1 | 2/2013 | Karalis et al. | |
| 2013/0057364 A1 | 3/2013 | Kesler et al. | |
| 2013/0062966 A1 | 3/2013 | Verghese et al. | |
| 2013/0069441 A1 | 3/2013 | Verghese et al. | |
| 2013/0069753 A1 | 3/2013 | Kurs et al. | |
| 2013/0099587 A1 | 4/2013 | Lou et al. | |
| 2013/0154389 A1 | 6/2013 | Kurs et al. | |
| 2013/0159956 A1 | 6/2013 | Verghese et al. | |
| 2013/0175874 A1 | 7/2013 | Lou et al. | |
| 2013/0175875 A1 | 7/2013 | Kurs et al. | |
| 2013/0200721 A1 | 8/2013 | Kurs et al. | |
| 2013/0221744 A1 | 8/2013 | Hall et al. | |
| 2013/0278073 A1 | 10/2013 | Kurs et al. | |

(56) References Cited

U.S. PATENT DOCUMENTS

| | | |
|---|---|---|
| 2013/0278074 A1 | 10/2013 | Kurs et al. |
| 2013/0278075 A1 | 10/2013 | Kurs et al. |
| 2013/0300353 A1 | 11/2013 | Kurs et al. |
| 2013/0307349 A1 | 11/2013 | Hall et al. |
| 2013/0320773 A1 | 12/2013 | Schatz et al. |
| 2013/0334892 A1 | 12/2013 | Hall et al. |
| 2014/0002012 A1 | 1/2014 | McCauley |
| 2014/0021798 A1 | 1/2014 | Kesler et al. |
| 2014/0035378 A1 | 2/2014 | Kesler et al. |
| 2014/0035704 A1 | 2/2014 | Efe et al. |
| 2014/0044281 A1 | 2/2014 | Ganem et al. |
| 2014/0044293 A1 | 2/2014 | Ganem et al. |
| 2014/0049118 A1 | 2/2014 | Karalis et al. |
| 2014/0191593 A1 | 7/2014 | Moh |

OTHER PUBLICATIONS

Schuder, John C. "Powering an Artificial Heart: Birth of the Inductively Coupled-Radio Frequency System in 1960," Artificial Organs, 26(11):909-915, Blackwell Publishing, Inc., Jun. 2002.

PCT International Search Report and Written Opinion for PCT Application PCT/US2012/065553, dated Mar. 20, 2013 (13 pages).

Schuder et al, Energy Transport to a Coil Which Circumscribes a Ferrite Core and Is Implanted Within the Body, IEEE Transactions on Bio-Medical Engineering, Jul./Oct. 1965, pp. 154-163, vol. BME-12, Nos. 3 and 4.

Hochmair, System Optimization for Improved Accuracy in Transcutaneous Signal and Power Transmission, IEEE Transactions on Biomedical Engineering, Feb. 1984, pp. 177-186, vol. BME-31, No. 2.

Fei Zhang, Steve A. Hackworth, Xiaoyu Liu, Haiyan Chen, Robert J. Sclabassi, and Mingui Sun, "Wireless Energy Transfer Platform for Medical Sensors and Implantable Devices", 31st Annual International Conference of the IEEE EMBS, Minneapolis, MN, USA, Sep. 2-6, 2009, pp. 1045-1048.

PCT Chapter I International Preliminary Report on Patentability (IPRP Chapter I) PCT/US2012/065553 dated May 27, 2014.(9 Pages).

PCT International Written Opinion for PCT International Appln No. PCT/US2005/022535 dated May 21, 2014. (7 pages).

PCT International Search Report PCT International Appln No. PCT/US2012/065553 dated May 30, 2013. (4 pages).

N. de N. Donaldson, Comments on "Efficient Transdermal Links With Coupling-Insensitive Gain", Apr. 198, pp. 280-281, IEEE Transactions on Biomedical Engineering, vol. 35, No. 4.

Douglas C. Galbraith et al, "A Wide-Band Efficient Inductive Transdermal Power and Data Link With Coupling Insensitive Gain", Apr. 1987, pp. 265-275, IEEE Transactions on Biomedical Engineering, vol. BME-34, No. 4.

Joe C. Stark III, "Wireless Power Transmission Utilizing a Phased Array of Tesla Coils", Thesis, May 2004, 247 pages, Submitted to the Department of Electrical Engineering and Computer Science in Partial Fulfillment of the Requirements for the Degree of Masters of Engineering in Electrical Engineering at the Massachusetts Institute of Technology.

Translation of Japanese Office Action dated Nov. 8, 2016 for JP Appln No. 2014-543508 (5 pages).

Extended European Search Report for counterpart EP Patent Application No. 19156259.4, 9 pgs. (dated Aug. 6, 2019).

\* cited by examiner

TRANSCUTANEOUS POWER TRANSMISSION UTILIZING NON-PLANAR RESONATORS

This application is a continuation of co-pending U.S. application Ser. No. 14/796,983 filed on Jul. 10, 2015, which is a continuation of U.S. patent application Ser. No. 13/301,717 filed on Nov. 21, 2011 (now issued as U.S. Pat. No. 9,079,043).

FIELD

Embodiments of the invention relate to wireless energy transfer; and more specifically, to the transfer of energy from a power source outside the body to an implanted medical device inside the body.

BACKGROUND

In wireless energy transmission systems, resonators with planar geometries have been used in the power transmitter and receiver units to facilitate the transfer of energy. Such planar resonators have geometries that span a substantially flat surface with no dimensional measurement on an axis orthogonal to the flat surface, or where dimensions on an axis along the flat surface are orders of magnitude greater than a dimension on an axis orthogonal to the flat surface. Transmission of power between the transmitter and receiver units relies on inductively or magnetically coupling the respective planar resonators. When the planar transmitter resonator carries an electrical current driven by an external power source, magnetic flux is generally generated in a direction perpendicular to the plane of the transmitter resonator. A planar receiver resonator is then placed within a vicinity of the planar transmitter resonator and is oriented parallel to the planar transmitter resonator such that the planar receiver resonator is able to effectively intercept the magnetic flux generated by the transmitter resonator to produce an electrical current in the receiver unit.

The use of planar resonators is an effective approach for closely coupled wireless power transmission systems to transfer energy between two stationary objects that are in close proximity. For example, in charging pad applications, a planar transmitter resonator is embedded in a charging pad that is placed on a desk. When an electronic device, such as a cellular phone, is equipped with a planar receiver resonator, and is placed on the charging pad, the two planar resonators are orientated parallel to each other along the planes of the resonators. In this parallel orientation, energy can be effectively transferred from the planar transmitter resonator embedded in the charging pad to the planar receiver resonator in the electronic device to charge the electronic device. Because the electronic device is not expected to move on its own, the two planar resonators remain oriented parallel to each other to continuously charge the electronic device until the electronic device is removed from the charging pad.

SUMMARY

The present invention is directed to a system for omni-orientational wireless energy transfer. The system may be particularly useful in applications where energy is to be transferred wirelessly between two objects, and at least one of the objects is free to move around. One such application is where energy is being transferred from a power transmitter unit to a receiver unit that is part of an implanted medical device. In such an application, while the transmitter unit may be stationary, for example, be plugged into a wall, a patient implanted with the medical device and the receiver unit may be free to move around such that the relative orientation of the transmitter and receiver units is not fixed and may change.

In one aspect of the present invention, a system for wireless energy transfer includes a transmitter unit and a receiver unit. The transmitter unit has a resonator with a coil configured to be coupled to a power supply to wirelessly transmit power to a receiver unit. The receiver unit has a resonator with a coil coupled to a device load. At least one of the resonators is a non-planar resonator that spans a non-degenerate two-dimensional surface with at least one concave portion.

In another aspect of the present invention, a method for omni-orientational wireless energy transfer includes the following steps. A resonator including a coil coupled to a power supply is provided. Another resonator with a coil coupled to an electrical load is placed at a separation distance from the other resonator. At least one of the resonators spans a non-degenerate two-dimensional surface with at least one concave portion to enable wireless energy transfer between the coils regardless of their respective orientation.

In a further aspect of the present invention, a transmitter unit for use in an omni-orientational wireless energy transfer system to wirelessly transfer energy to a receiver unit includes a non-planar resonator with a coil that spans a non-degenerate two-dimensional surface with at least one concave portion. The transmitter unit also includes power circuitry coupled to the coil. The power circuitry is configured to be electrically connected to a power supply source to deliver an electrical current to the coil.

In a different aspect of the present invention, a receiver unit for use in an omni-orientational wireless energy transfer system to receive wirelessly transferred energy from a transmitter unit includes a non-planar resonator with a coil that spans a non-degenerate two-dimensional surface with at least one concave portion. The receiver unit also includes an electrical load coupled to the coil.

BRIEF DESCRIPTION OF THE DRAWINGS

The invention may best be understood by referring to the following description and accompanying drawings that are used to illustrate embodiments of the invention. In the drawings.

DESCRIPTION OF EMBODIMENTS

Figure 1:
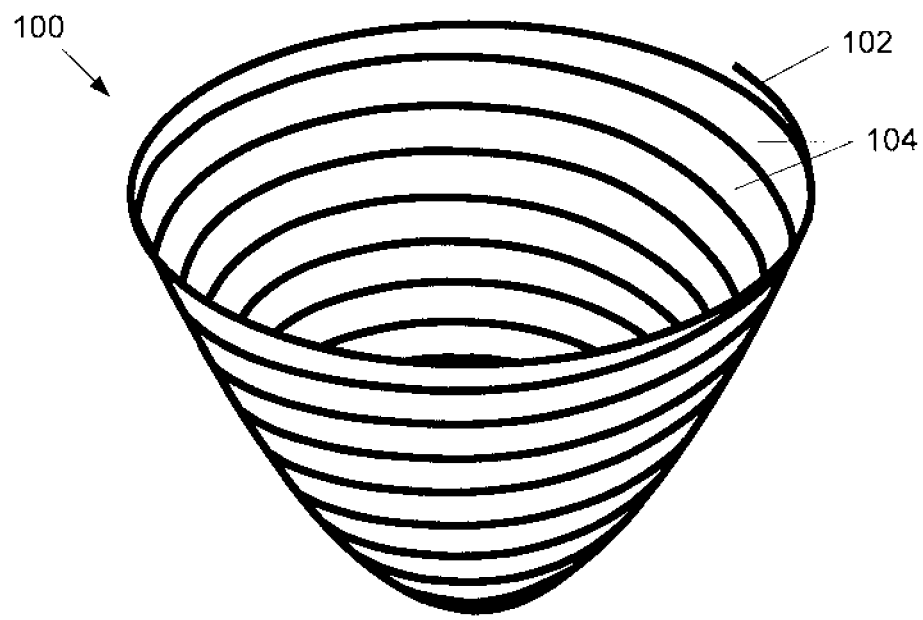
FIG. 1 illustrates a non-planar resonator according to one embodiment of the invention.

In the following description, numerous specific details are set forth. However, it is understood that embodiments of the invention may be practiced without these specific details. In other instances, well-known circuits, structures and techniques have not been shown in detail in order not to obscure the understanding of this description.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In the following description and claims, the terms "coupled" along with its derivatives, may be used. It should be understood that the term "coupled" is used to indicate that two or more elements, which may or may not be in direct physical or electrical contact with each other, co-operate or interact with each other. The terms "energy transfer," "power transfer," and "power transmission," and their derivatives, are used interchangeably and refers to the transmission of energy between two devices.

Although the use of planar resonators is effective for applications that transfer power between two stationary objects, as the transmitter and receiver resonators are moved or rotated into a non-parallel orientation, the rate of power transfer dramatically decreases. Even in systems that are capable of transmitting power over large separation distances, no net power transfer will occur when the planar transmitter resonator is orientated orthogonal to the planar receiver resonator. Thus, in systems where the relative orientation of the transmitter and receiver devices may vary greatly or is unknown, it is possible for the receiver device to receive no power at all for an extended period of time when the planar resonators are positioned orthogonal to each other. While this result may be inconsequential in certain applications, this result may pose a risk to the health of a patient if the receiver device is an implanted medical device that is used to assist critical bodily functions, and a power storage unit, such as a battery, in the implanted medical device is not promptly recharged.

An implanted medical device can be powered or charged using a transcutaneous energy transfer system (TETS) that transfers electrical energy from an external power source to the implanted medical device wirelessly through the skin of a patient. In a conventional TETS that uses planar resonators, a patient is restricted to remain substantially in a fixed or known position relative to a power transmitter device in order to sustain effective power transmission over an extended period of time. For example, suppose a patient is implanted with a medical device with a planar receiver resonator and is resting on a bed. A planar transmitter resonator can be positioned on or embedded in the bed such that when the patient is laying flat on the patient's back, the two resonators are oriented substantially parallel to each other to effect charging of the implanted medical device while the patient rests. However, as the patient moves or rolls around in bed, the amount of power transfer between the planar transmitter resonator and the planar receiver resonator implanted in the patient can drop to zero if the patient turns to rest on the patient's side such that the resonators are now orthogonal to each other. If the patient does not move from this position for an extended period of time, the implanted medical device may lose power completely to pose a risk to the patient.

In accordance to one embodiment of the present invention, a non-planar resonator to enable omni-orientational wireless energy transfer in a wireless energy transmission system will now be described. A non-planar resonator is a resonator that spans a surface area occupying three spatial dimensions instead of two dimensions. For example, in one embodiment, the non-planar resonator is a resonator that spans a non-degenerate two-dimensional surface with at least one concave portion, such as an elliptical paraboloid surface. An elliptical paraboloid surface is surface that is shaped like a bowl, with the interior of the bowl being the concave portion. It should be noted that in an elliptical paraboloid surface, when the concave portion is extended along the elliptical paraboloid surface, the concave portion can extend out to infinite space. In other words, the concavity of the elliptical paraboloid surface does not wrap around and does not enclose on itself. In three-dimensional Euclidian space, an elliptical paraboloid surface is described by the equation:

$$x^2/a^2 + y^2/b^2 - z = 0, \text{ where } a \text{ and } b \text{ are constants.}$$

In an exemplary embodiment as shown in FIG. 1, the non-planar resonator 100 spanning an elliptical paraboloid surface has a spiral wire coil 102, such as a Litz wire coil, that starts at the center of the bottom of an imaginary bowl-shaped surface defined by the above equation, and spirals upwards along the sidewalls of the surface up to the rim of the imaginary bowl-shaped surface.

In some embodiments, there can be gaps 104 in between the loops of the spiral wire coil 102. The gaps 104 can be uniformly distributed, or there can be portions of the wire coil that have wider gaps and other portions that have narrower gaps. Similarly, the density of the wire windings can also vary over the surface of the non-planar resonator 100. The geometries of the gaps and the density of the wire windings can be used to tailor the non-planar resonator to have a specific inductance or a specific capacitance to achieve a particular resonant frequency. It should be understood that this is just one example of a wire coil configuration that forms a resonator spanning a non-planar surface. In other embodiments, the wire coil 102 can be configured differently to form a resonator that spans such a surface.

Figure 2:
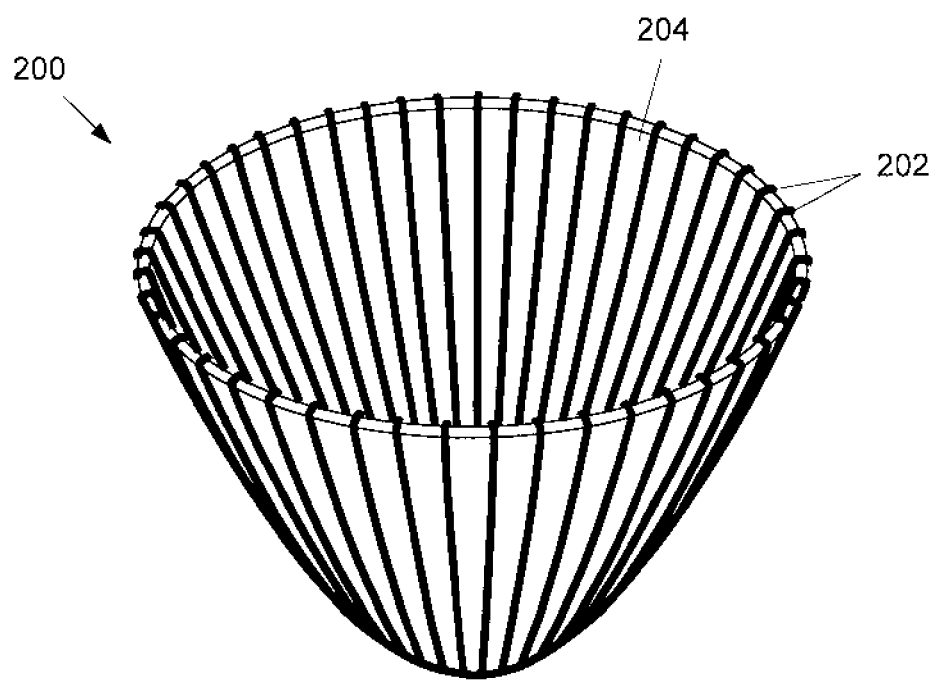
FIG. 2 illustrates a non-planar resonator according to another embodiment of the invention.

Alternatively, as shown in FIG. 2, the non-planar resonator 200 can be an elliptical paraboloid or bowl-shaped core 204 made of a magnetic material to direct magnetic flux. A wire 202, such as a Litz wire, for purpose of exemplary illustration, is wrapped around that core 204. The wire 202 can be wrapped around the core 204 from one side of the bowl-shaped core 204 to an opposing side, be wrapped around the exterior surface of the bowl-shaped core 204, or be wrapped along intersecting diameters of the bowl-shaped core 204 as shown. In other embodiments, the wire 202 can be wrapped around the magnetic core 204 in other configurations. As with the above embodiment, the density of the wire windings can be tailored to achieve a particular resonant frequency.

In another exemplary embodiment, the non-planar resonator spans a non-degenerate two-dimensional surface that has at least two concave portions, such as a hyperbolic paraboloid surface. A hyperbolic paraboloid surface is a surface that is shaped like a saddle, with the top of the saddle being one concave portion and the bottom of the saddle being another concave portion. In one embodiment, the concave curvature of one concave portion can be orthogonal to the concave curvature of the other concave portion. It should be noted that in a hyperbolic paraboloid surface, when the concave portions of the surface are extended along the hyperbolic paraboloid surface, the concave portions can extend out to infinite space. In other words, the concavities of the hyperbolic paraboloid surface do not wrap around and do not enclose on themselves. In three-dimensional Euclidian space, a hyperbolic paraboloid surface is described by the equation:

$$x^2/a^2 - y^2/b^2 - z = 0, \text{ where } a \text{ and } b \text{ are constants.}$$

Figure 3:
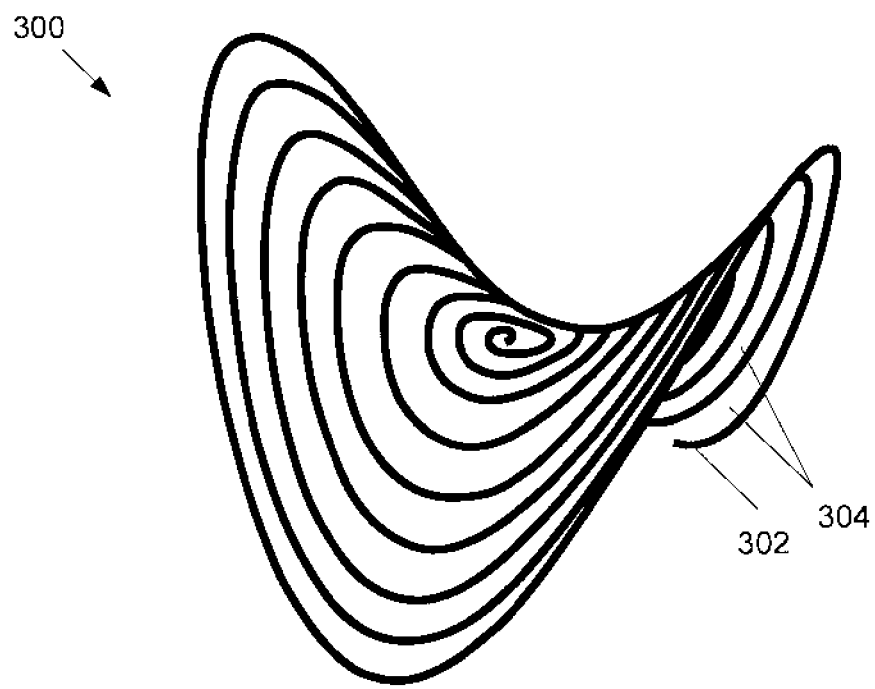
FIG. 3 illustrates a non-planar resonator according to a further embodiment of the invention.

In one embodiment as shown in FIG. 3, the non-planar resonator 300 spanning a hyperbolic paraboloid surface has a spiral wire coil 302, such as a Litz wire coil, that starts at the center of an imaginary saddle-shaped surface and spirals outwards along the saddle-shaped surface. In some embodiments, there can be gaps 304 in between loops of the spiral wire coil 302. In other embodiments, the wire coil 302 can be configured differently to form a resonator that spans such a surface. The geometries of the gaps 304 and the density of the wire windings can also be used to tailor the non-planar resonator to have a specific inductance value or a specific capacitance value to achieve a particular resonant frequency.

Figure 4:
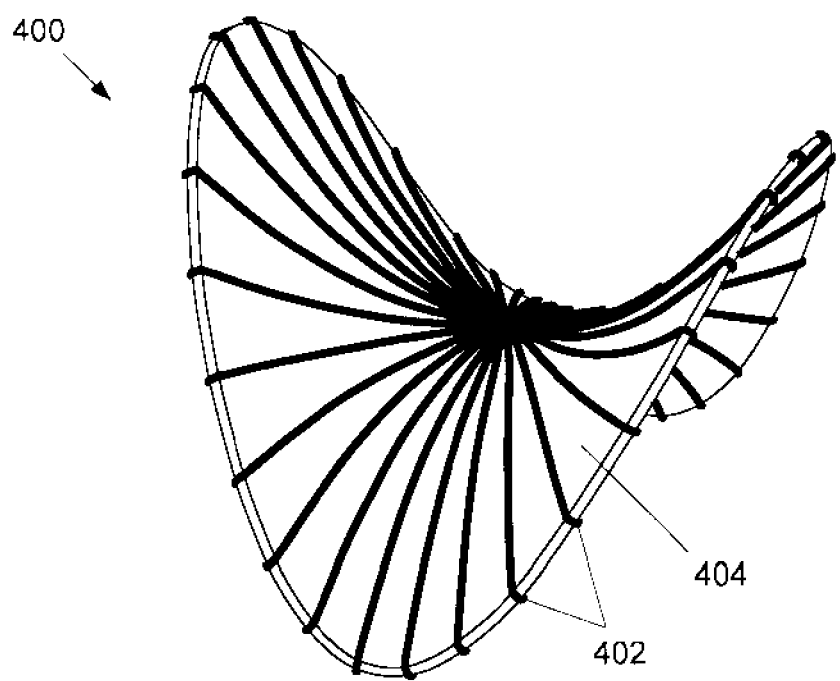
FIG. 4 illustrates a non-planar resonator according to a different embodiment of the invention.

Alternatively, as shown in FIG. 4, the non-planar resonator 400 can be a hyperbolic paraboloid or saddle-shaped core 404 made of a magnetic material to direct magnetic flux. A wire 402, such as a Litz wire, is wrapped around that core 404. The wire 402 can be wrapped around the core 404 from one side of the saddle-shaped core 404 to an opposing side, or be wrapped across the center of the saddle-shaped core 404 as shown. In other embodiments, the wire 402 can be wrapped around the magnetic core 404 in other configurations. As with the other embodiment, the density of the wire windings can be tailored to achieve a particular resonant frequency.

More generally, a non-planar resonator according to embodiments of the present invention is a resonator that span a non-degenerate two-dimensional surface defined by one of the following equations in three-dimensional Euclidean space:

$$Ax^2 + By^2 + Cz^2 = D, \text{ or}$$

$$Ax^2 + By^2 + Cz = 0, \text{ where } A, B, C, \text{ and } D \text{ are non-zero numbers.}$$

Surfaces defined by these equations are sometimes referred to as non-degenerate quadric surfaces. In addition to the elliptical paraboloid and hyperbolic paraboloid surfaces described above, another exemplary embodiment of a non-planar resonator that spans a surface defined by one of the above equations includes a non-planar resonator that spans a hyperboloid surface. One feature of such surfaces is that these surfaces have a parabolic cross section. A non-planar resonator according to embodiments of the present invention can be implemented with a wire coil that is formed to outline the shape of a non-degenerate two-dimensional surface. The wire that is used to form the coil can be, for example, a Litz wire. A Litz wire is generally referred to as a type of cable used in electronics to carry electric current and may have many individually braided or woven strands of wire in one or more patterns at one or more levels to increase the amount of current passing through each cable by increasing surface area and decreasing the resistance. Alternatively, the wire can be a strand or foil of conductive metal (e.g., such as copper, gold, or silver) with an insulated covering. In other embodiments, the non-planar resonator can be implemented with a wire, for example, a Litz wire, that is wrapped around a core of magnetic material, where the magnetic core has been molded or formed to have a non-degenerate two-dimensional surface. In these embodiments, the core of magnetic material is used to direct magnetic flux in various directions depending on the shape of the magnetic core. In some embodiments, the resonant frequency of the resonator can be in a range of 100 kHz to 10 MHz.

As indicated by the embodiments described above, the phrase that "a resonator spans a non-degenerate two-dimensional surface," and similar derivatives, do not necessary require the resonator to have a solid surface. Instead, as used herein, the phrase that a resonator spans a non-degenerate two-dimensional surface can mean that the resonator forms an outline of such a surface (e.g., the spiral coil), or mean that the resonator has such a surface (e.g., the magnetic core with a wire wrapped around the core). Furthermore, it should be noted that the phrase that "a resonator spans a non-degenerate two-dimensional surface," and similar derivatives, also mean that the shape of the resonator may have minor features or deformalities that may deviate from such a surface, without departing from the spirit of the present invention. For example, with respect to the embodiment with the elliptical paraboloid bowl-shaped surface, the resonator may have a flat bottom instead of a curved bottom, or the sidewall may have one or more minor dimple indentations. It should be understood that such minor features or deformalities do not detract away from the scope and spirit of the exemplary embodiments.

Figure 5:
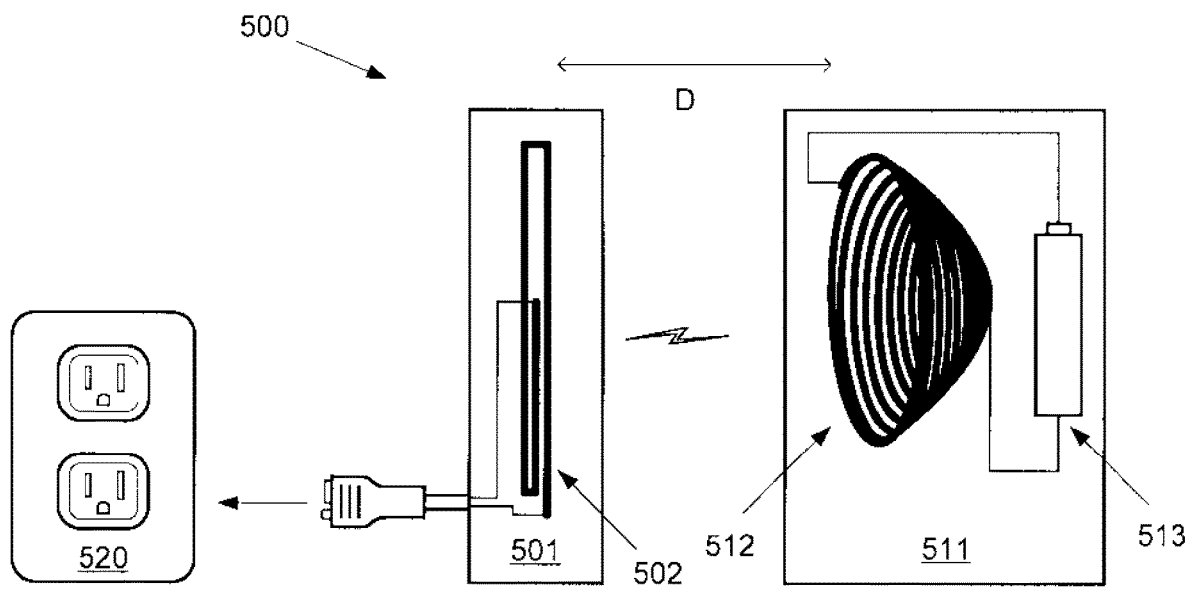
FIG. 5 illustrates a conceptual diagram of a system for wireless energy transfer according to one embodiment of the invention.
Figure 6:
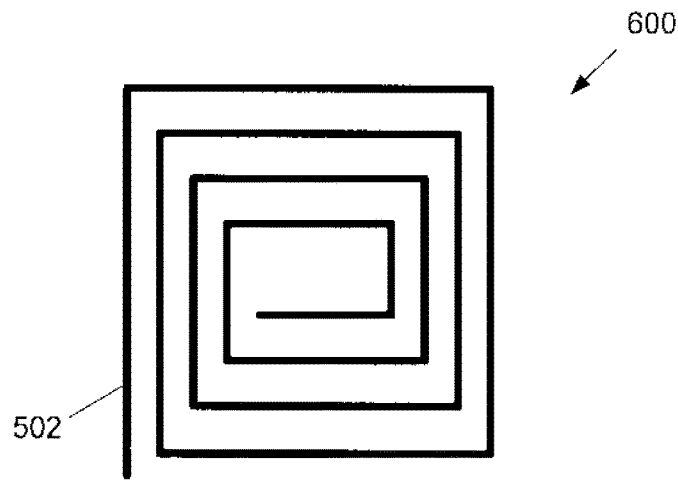
FIG. 6 illustrates a planar resonator used in a system for wireless energy transfer according to an embodiment of the invention.

FIG. 5 illustrates an omni-orientational wireless energy transfer system 500 according to one embodiment of the present invention. The omni-orientational wireless energy transfer system 500 includes a transmitter unit 501 that has a transmitter resonator 502 with a wire coil, and a receiver unit 511 that has a receiver resonator 512 with a wire coil. In this particular embodiment as shown, the receiver resonator 512 is a non-planar resonator that spans an elliptical paraboloid surface. In other embodiments, the receiver resonator 512 may span any of the non-degenerate two-dimensional surfaces described above. Furthermore, while in the embodiment as shown in FIG. 5, it is the receiver unit that has a non-planar resonator, in other embodiments, it can be the transmitter unit or both the receiver and transmitter units that have a non-planar resonator.

In the exemplary omni-orientational wireless energy transfer system 500 shown in FIG. 5, the transmitter resonator 502 is a planar resonator. A planar top view 600 of the transmitter resonator 502 is shown in FIG. 7. As shown, the wire that forms the transmitter resonator 502 in the transmitter unit 501 spans a planar surface. More specifically, the transmitter resonator 502 in this exemplary embodiment is a square spiral wire coil with each loop of the spiral wire coil arranged in substantially the same plane as each other. In other embodiments, other planar transmitter resonators may be used.

The transmitter unit 501 is configured to be coupled to a power supply or a power source 520, for example, a wall electrical outlet, such that when the transmitter unit 501 is powered, the power source 520 drives an electrical current through the coil of the transmitter resonator 502. Alternatively, the transmitter unit 501 can be coupled to other power sources such as a battery that can be used to drive an electrical current through the coil of the transmitter resonator 502. Consequently, magnetic flux perpendicular to the plane of the planar transmitter resonator 502 is generated by the electrical current running through the coil of the transmitter resonator 502. Although not shown, it should be understood that the transmitter unit 501 may have additional power circuitry, for example, to perform alternating current (AC) to direct current (DC) conversion, or vice versa, and may have additional control circuitry, for example, to modulate the power output of the transmitter unit 501. When the receiver unit 511 is brought within an operating distance of the system, the magnetic flux generated from the transmitter unit 501 induces a current in the receiver resonator 512 in the receiver unit 511, which causes an electrical current to flow in the coil of the receiver unit 511. The coil in the receiver unit is coupled to an electrical or device load 513. The electrical current flowing through the coil in the receiver unit 511 can then be used to power the device load 513. In the case that the device load 513 is a battery or other types of rechargeable power storage device as shown, the electrical current flowing through the coil in the receiver unit 511 can be used to recharge the power storage device. In this manner, the omni-orientational wireless energy transfer system 500 is able to wirelessly transfer power from the transmitter unit 501 to the receiver unit 511.

By using resonators in the transmitter and receiver units 501 and 511 that have closely matched resonant frequencies, the power transfer efficiency of the system 500 can be improved, and consequently, the range of distances of the omni-orientational wireless energy transfer system 500 through which power can be transferred can be extended beyond conventional inductive coupling techniques. A resonator is an object that has a natural oscillation frequency. More specifically, with respect to wireless energy transfer, a resonator is an object that stores energy in two forms and exchanges the stored energy between the two forms continuously. In an electromagnetic resonator, stored energy is continuously being exchanged or oscillating between the electric fields of a capacitive element and the magnetic field of an inductive element. The oscillation decays or dampens due to resistive losses in the resonator. Because of this oscillation, energy that is not transferred from a transmitter to a receiver in one cycle of the oscillation is not lost completely. In other words, the stored energy in a transmitter can be transferred to a receiver through many cycles of the oscillation. This is in contrast to a pure inductive coupling system where any energy stored in the magnetic field of an inductive element that is not transferred to a receiver at an instance is lost. At large separation distances, this energy loss in a pure inductive coupling system is significant and results in little or no meaningful amount of energy being transferred. In the wireless energy transfer system 500, the use of resonators allows most of the stored energy in the transmitter unit 501 to be transferred to the receiver unit 511 over many oscillation cycles as described above to improve the overall power transfer efficiency of the system 500. As a result, the receiver unit 511 can be placed at a separation distance further away from the transmitter unit 501 and still allows a meaningful amount of energy to be transferred over time.

While resonators have been used in wireless energy transfer systems to extend the communication/transfer range of the systems, the systems that use planar resonators are susceptible to changes in the relative orientation of the resonators with respect to each other. A comparison of a system that uses a non-planar resonator to a system that uses a planar resonator with both systems having the same separation distance and rated for the same output power may be as follows. The amount of energy that is received at the receiver in the non-planar resonator system in a particular direction can potentially be less than the amount of energy that is received at the receiver in a planar resonator system when the transmitter and receiver resonators are parallel to each other. In an exemplary embodiment, the amount of energy that is received in the non-planar resonator system can be about 25% of the amount of energy that is received in the planar resonator system when the planar resonator system is arranged in its preferred orientation (when the transmitter and receiver resonators are parallel to each other). However, although a planar resonator may be able to transfer more power in a single preferred orientation, the amount of energy that a planar resonator system can transfer drops off dramatically when the system is arranged in other orientations and can drop to zero when the orientation of the transmitter and receiver resonators are arranged orthogonal to each other.

By using a non-planar resonator 512 that spans a surface area occupying three spatial dimensions, for example, in the receiver unit 511, the same transmitter unit 501 is able to couple or transfer energy to the non-planar receiver resonator 512 over a wider range of spatial orientations as compared to a receiver unit having a planar resonator. Hence, at a given separation distance D that is within an operating range of the omni-orientational wireless energy transfer system 500, there is no requirement that the resonators 502 and 512 have to be placed in any particular orientation with respect to each other in order to transfer a meaningful amount of power required to power or recharge the device load 513. In one exemplary embodiment, the system 500 is able to achieve a power transfer between the transmitter resonator 502 and the non-planar receiver resonator 512 at a given separation distance D that is at least 25% of a maximum power transfer (compared to a planar receiver resonator) at that given separation distance D, regardless of the orientation of the transmitter resonator 502 relative to the non-planar receiver resonator 512. For example, in an embodiment, power in the range of 5 W to 20 W can be transferred from the transmitter resonator 502 to the receiver resonator 512 over a separation distance D in the range of, for example, 2.5 cm to 35 cm. The system 500 is able to transfer a maximum about of 20 W at a distance D of 10 cm when the resonators 502 and 512 are in their ideal alignment. Even when the resonators 502 and 512 are rotated or displaced from their ideal alignment, the system 500 is still able to transfer at least 5 W of power to the receiver unit 511 at the same distance D of 10 cm. In other embodiments, a greater or lesser amount of power can be delivered over other distances by adjusting the size and geometries of the resonators. The same concept of using non-planar resonators is independent of distance and can equally apply in a larger range of distances so long as there is sufficient power for the signal to travel that range.

In some embodiments, the resonant frequency of the transmitter resonator 502 can be 100 kHz, 500 kHz, 1 MHz, or 10 MHz. The receiver resonator 512 is designed to have a resonant frequency that closely matches the transmitter resonator 502. Hence, if the transmitter resonator 502 has a resonant frequency of 100 kHz, the receiver resonator is designed to also have a resonant frequency close to 100 kHz, for example, within ±5% or ±10% of 100 kHz. In other embodiments, the resonant frequency of the closely matched resonators 502 and 512 can be a frequency that is in the range of 100 kHz to 10 MHz. In further embodiments, other resonant frequencies can be used.

In the embodiment as shown in FIG. 5 and as described above, the transmitter and receiver resonators 502 and 512 are shaped differently. Even if both resonators are made of the same materials with the same length of wire, each resonator may have a slightly different natural resonant frequency due to differences in their geometries and configurations. In addition, other factors that may cause the resonant frequency of one resonator to deviate from the resonant frequency of the other resonator include differences in the surrounding environment of the resonator. For example, one resonator may be subjected to a different temperature than the other resonator, or one resonator may be subjected to other extraneous objects that may affect the resonant frequency, such as a nearby sheet of highly conductive material.

To improve the performance of the system, a tunable capacitor can be coupled to the coil of at least one of the resonators. A tunable capacitor is a circuit or component with a variable capacitance value that can be changed in response to a control input. The control input may be voltage, current, frequency, or any other input that can cause the materials or circuit of the tunable capacitor to change its capacitance value. Coupling a tunable capacitor to the coil enables the effective capacitance value of the resonator to be adjusted. By adjusting the effective capacitance value of the resonator using the tunable capacitor, the resonant frequency of that resonator can be tuned to match the resonant frequency of the other resonator of the system and to maximize a voltage gain at the receiver unit 511. Furthermore, not only can the tunable capacitor be used to match the resonant frequencies of the resonators, the tunable capacitor can also be used to detune the system to reduce the amount of energy transferred from the transmitter unit 501 to the receiver unit 511 if the operating conditions of the system require less energy to be transferred. In other embodiments, an array or network of capacitive elements can be coupled to the coil of at least one of the resonators to tune the resonant frequency of the system. The array or network of capacitive elements can be configured to form different series and/or parallel arrangements of capacitive elements to achieve an effective capacitance value for the resonator for the same purposes as described above. Alternatively, a tunable or network of inductive elements can be used to adjust the effective inductance of the resonator to change the resonant frequency.

In a further embodiment, at least one of the resonators 502 and 512 is coupled to a tunable resistor or an array or network of resistive elements to tune a quality factor "Q" of the system to maximize a voltage gain at the receiver unit 511. A tunable resistor is a circuit or component with a variable resistance value that can be changed in response to a control input. The control input may be voltage, current, or any other input that can cause the materials or circuit of the tunable resistor to change its resistance value. Similarly, an array or network of resistive elements can be configured to form different series and/or parallel arrangements of resistive elements to achieve an effective resistance value. For example, the resistive elements can be resistors, capacitors with effective resistance values, or a combination of both. In an embodiment, an array of resistive elements can be an array of capacitors, where the capacitors have the same capacitance values but different effective series resistance values. This allows the effective resistance to be adjusted while keeping the effective capacitance the same.

The quality factor "Q" describes the inverse power loss of the resonator. Hence, a larger Q means a lower power loss in the resonator and a higher energy transfer efficiency, resulting in a higher voltage gain at the receiver unit 511. The quality factor "Q" of a resonant system that has a transmitter resonator 502 and a receiver resonator 512 can be described by the square root of the product of the quality factors of the two resonators 502 and 512. In order to reduce the power loss in the system 500 to maximize the voltage gain at the receiver unit 511, the quality factor "Q" of the system can be increased by increasing the quality factors of either or both resonators 502 and 512. This can be achieved by tuning a tunable resistor or an array of resistive elements that is coupled to the coil of the respective resonator to modulate and to match the impedance seen by the resonator. Alternatively, a tunable or network of capacitive and/or inductive elements can be used to adjust the effective capacitance and/or the effective inductance to change the quality factor "Q."

In another embodiment, the power transfer efficiency of the system can be further improved by using a flux concentrator made of high-permeability, low-loss materials to direct the output magnetic flux generated from the transmitter unit 501 towards the receiving unit 511. In embodiments that lack a flux concentrator, the magnetic flux generated from the transmitter coil is spread around the transmitter coil, even in stray directions that are away from the receiving unit 511. The use of a flux concentrator on the transmitter unit 501 can create a magnetic path to channel and redirect the generated magnetic flux from those stray directions towards the direction of the receiving unit 511. Similarly, a flux concentrator can also be used in the receiving unit 511 to redirect magnetic flux around the surrounding areas of the receiver coil towards the receiver coil.

To facilitate the tuning of the system using the techniques and components described above, each of the transmitter unit 501 and the receiver unit 511 may include additional communications circuitry such as encoders, decoders, antennae, amplifiers, modulators, and filters, to establish a communications channel between the receiver unit 511 and the transmitter unit 501 to communicate system information between the units to adjust the components in order to modulate the power delivered to the receiver unit 511. For example, wireless communications channel can be a radio frequency signal or other wireless signal transmissions including Wi-Fi (IEEE 802.11 family), Bluetooth, infrared, and other well-known wireless communications protocols. The system information communicated over the communications channel can include performance data such as the battery level and usage of the device load 513. Other performance data may include the resonant frequencies, the impedances of circuits in the system, the voltages and loads of the system, the temperature of the resonators 502 and 512, and other data that can be used to tune and detune the system. In addition, the system information communicated over the communications channel may also include identification information of the transmitter and receiver units 501 and 511, as well as commands to change the system's settings or operating modes.

While the above embodiments have been described with the receiver unit 511 having a non-planar resonator, in other embodiments, the non-planar resonator spanning the non-degenerate two-dimensional surface can be in both the transmitter unit 501 and the receiver unit 511, or only in the transmitter unit 501, because of the symmetry in the resonant coupling of the resonators. Hence, as long as at least one of the receiver or transmitter resonators is a non-planar resonator that spans a non-degenerate two-dimensional surface, power can be transmitted at a given operating distance regardless of one resonator's orientation relative to the other resonator. This symmetrical property of the system is particularly useful in applications where space is limited in the receiver unit or where other factors such as extraneous objects restrict the types of geometries that can be used in the receiver resonator.

One example of such an application is a transcutaneous energy transfer system (TETS), where the receiver unit is part of an implanted medical device. For an implanted medical device such as a ventricular assist device or a blood pump, the receiver resonator is configured for subcutaneous placement within a human. Depending on the implant location of the receiver resonator in the human body, the geometry of the receiver resonator may be spatially restricted by the proximity of nearby organs or other body structure. Hence, in such applications, it may be desirable to have the non-planar resonator in the transmitter unit instead of the receiver unit. Different embodiments are also possible. For example, a non-planar resonator can be implanted in the thoracic/abdomen area, wrapping around a part of, or the entire circumference of the body of a patient. The non-planar resonator can be formed to span a surface that takes after an undulating outline of the ribs and general shape that contours around the rib cage.

In an exemplary embodiment, the dimensions of a non-planar implanted receiver resonator may span a depth in a range of 0.5 inches (in.) to 2 in. and be no bigger than 3 in. by 3 in. along the largest possible area spanned by a cross section of the resonator. In other words, the implanted receiver resonator may span a volume that is less than 3 in. by 3 in. by 2 in. In other embodiments, the implanted receiver resonator can have the largest possible area spanned by a cross section of the resonator to be an area as big as the human anatomy can allow as with the case where a non-planar resonator wraps around the abdomen of the body.

Figure 7A:
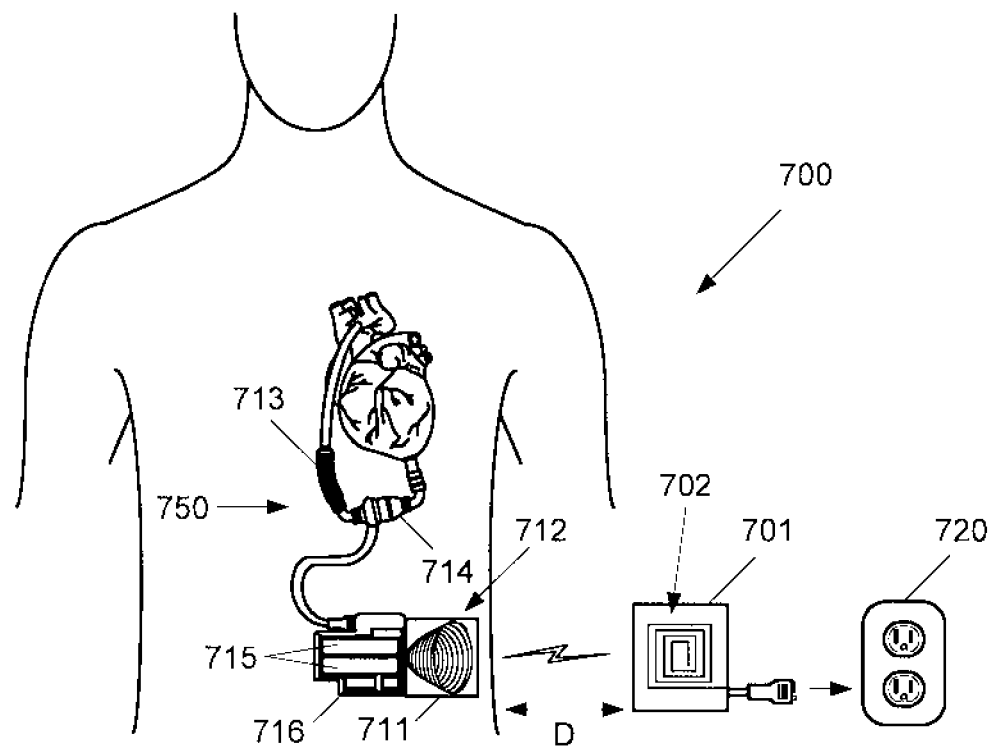
FIG. 7A illustrates a transcutaneous energy transfer system (TETS) according to one embodiment of the invention.
Figure 7B:
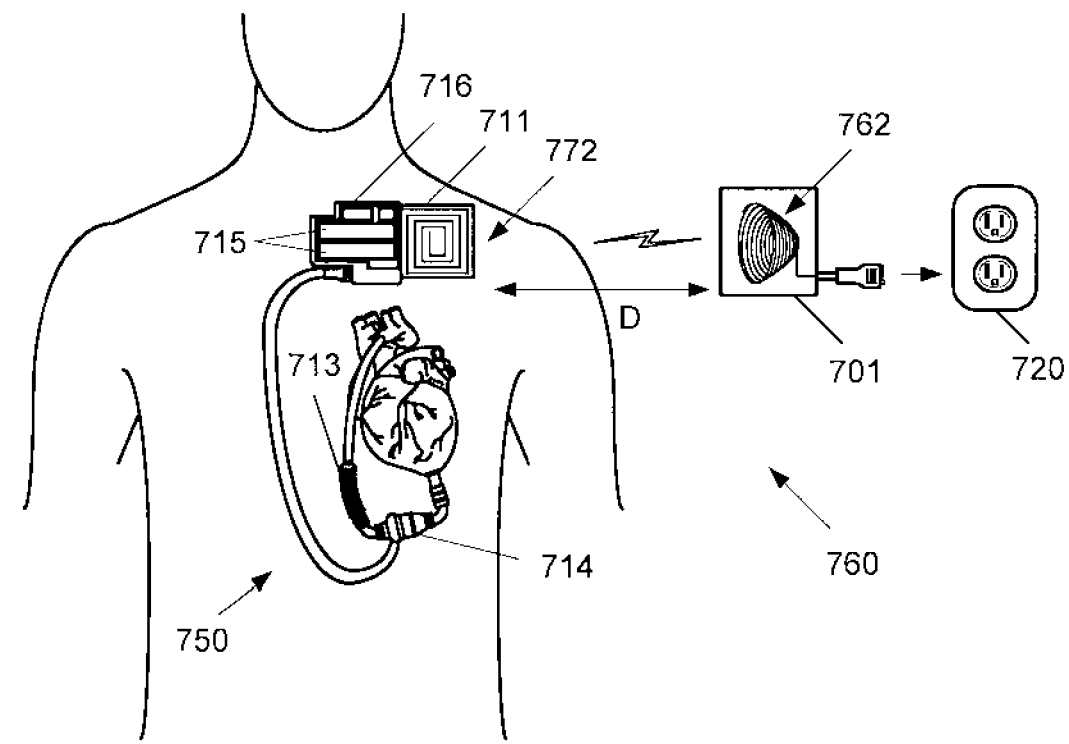
FIG. 7B illustrates a TETS according to another embodiment of the invention.

FIGS. 7A and 7B illustrates exemplary embodiments of a TETS 700 with a ventricular assist device (VAD) 750 according to embodiments of the present invention. A VAD is a mechanical circulatory device that is used to partially or completely replace the function of a failing heart. For patients suffering from congestive heart failure, the VAD is implanted into the patient for long term use. VADs are designed to assist either the right (RVAD) or left (LVAD) ventricle, or both at once (BiVAD). VADs can be designed with an axial flow or centrifugal flow configuration. An impeller configured in an axial flow or centrifugal configuration can be suspended by journal bearing such as a ball and cup, or by a combination of active and/or passive magnetic forces, or by a combination of passive magnetic forces and hydrodynamic forces. In other embodiments, the blood pump can be an artificial heart, which is designed to completely take over cardiac function and may require the removal of a patient's heart.

The VAD 750 includes a pump assembly 713, a blood pump 714, a rechargeable power storage device 716, and a power receiver unit 711. The rechargeable power storage device 716 may include two or more rechargeable batteries 715 to provide the VAD 750 with a backup battery in case the stored energy in the primary battery is depleted or if the primary battery fails otherwise. The rechargeable power storage device 716 can be implanted in a location away from the blood pump assembly 713, for example, in the lower abdominal as shown in FIG. 7A. The power receiving unit 711 includes a resonator 712 with a coil that is coupled to the power storage device 716, which is the electrical load of the power receiver unit 711. In the embodiment as shown in FIG. 7A, because the receiver unit 711 is implanted in the lower abdominal area where there may be less spatial constraints on the size and shape of the receiver resonator 712, the receiver resonator 712 is the non-planar one of the resonators in the TETS 700 and spans a non-degenerate two-dimensional surface including any of the surfaces described above. The resonant frequency of the receiver resonator 712 can be in a range of 100 kHz to 10 MHz. In an exemplary embodiment, the resonant frequency of the receiver resonator 712 can be 100 kHz, 500 kHz, 1 MHz, or 10 MHz. In other embodiments, another resonant frequency that is safe for the human body can be used.

The TETS 700 also includes a power transmitter unit 701 that is external to the patient. The transmitter unit 701 includes a transmitter resonator 702 with a coil that is configured to be coupled to a power supply source 720 such as an electrical wall outlet. Alternatively, the transmitter unit 701 can be coupled to other power sources such as a battery that can be used to drive an electrical current through the coil of the transmitter resonator 702. In this particular embodiment, the transmitter resonator 702 is a planar resonator made of a planar wire loop. When the transmitter unit 701 is plugged into the electrical wall outlet 720, an electrical current is generated in the coil of the transmitter resonator 702. The resonant frequency of the transmitter resonator 702 can be in a range of 100 kHz to 10 MHz. In an exemplary embodiment, the resonant frequency of the transmitter resonator 702 can be 100 kHz, 500 kHz, 1 MHz, or 10 MHz. In other embodiments, another resonant frequency that is safe for the human body can be used. The transmitter resonator 702 as part of the transmitter unit 701 may be embedded in a stationary object such as a wall, a chair, a bed, or other fixtures such as a car seat or objects that do not move by themselves without external control or human assistance. The source of power for a stationary and embedded transmitter resonator is generally alternating current from an electric outlet, but can also be direct current from a battery source. In other embodiments, the transmitter resonator 702 may be part of a piece of wearable clothing such as a vest or a jacket, or other wearable accessories. In the case of a transmitter resonator that is embedded into a piece of clothing or object wearable by a person that moves with a person, the source of power would be portable sized rechargeable batteries that also could be worn by the patient.

When the receiver unit 711 in the patient comes within a separation distance D of the transmitter unit 701, the TETS 700 is able to wirelessly transfer energy from the transmitter unit 701 to the receiver unit 711 to recharge the power storage device 716 of the VAD 750. In one embodiment, at a given separation distance D being in the range of 2.5 cm to 35 cm, the transmitter unit 701 is able to deliver power in the range of 5 W to 20 W to the receiver unit 711 to recharge the batteries 715 in the power storage device 716 of the VAD 750. By using a non-planar coil in the receiver resonator 712 in the receiver unit 711, the TETS 700 is able to achieve a power transfer between the transmitter coil in the transmitter resonator 702 and the receiver coil in the receiver resonator 712 at a given separation distance D that is at least 25% of a maximum achievable power transfer at that given separation distance D, regardless of the coils' respective orientation to each other. For example, in one embodiment, the TETS 700 is able to transfer a maximum amount of 20 W at a distance D of 10 cm when the respective coils in the receiver and transmitter resonators 702 and 712 are in their ideal alignment. As the patient moves around and causes the coil in the receiver resonator 712 to be orientated at a different angle relative to the coil in the transmitter resonator 702 away from their ideal alignment, the TETS 700 is still able to transfer at least 5 W of power to the receiver unit 711 at the separation distance D of 10 cm. In other embodiments, a greater or lesser amount of power can be delivered over longer distances, for example, separation distances of 35 cm and beyond, by adjusting the size and geometries of the resonators.

The use of a non-planar resonator that spans a surface area occupying three spatial dimensions in the receiver unit 711 according to embodiments of the present invention has the advantage over conventional systems that uses only planar resonators, in that the non-planar receiver resonator 712 is able to couple with more magnetic flux generated from the transmitter unit 701 in a wider range of spatial orientations. Hence, at a given separation distance D within an operating range of the TETS 700, there is no requirement that the resonators 702 and 712 have to be placed in a particular orientation with respect to each other in order to transfer a meaningful amount of power required to recharge the rechargeable storage device 716.

Figure 8A:
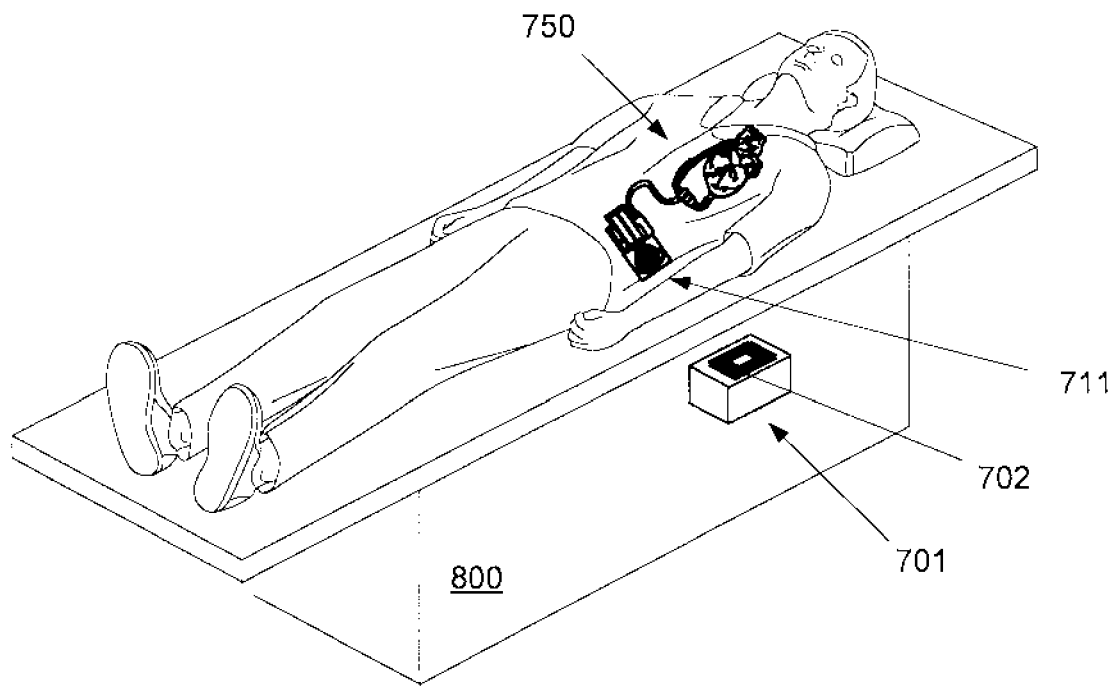
FIG. 8A illustrates a TETS arranged in a particular orientation according to an embodiment of the invention.
Figure 8B:
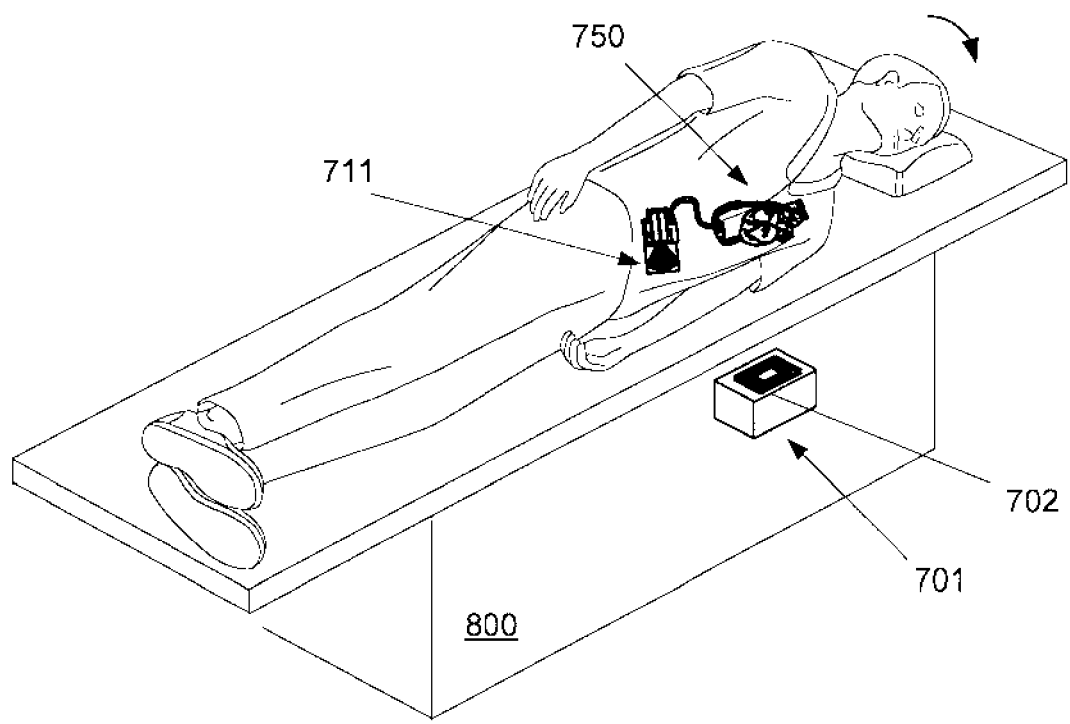
FIG. 8B illustrates a TETS arranged in a different orientation according to an embodiment of the invention.

This advantage of the TETS 700 according to an embodiment of the present invention is illustrated in FIGS. 8A and 8B. In FIGS. 8A and 8B, the transmitter resonator 702 as part of the transmitter unit 701 of the TETS 700 is embedded in a bed 800. Implanted in a patient are a VAD 750 and a receiver unit 711 with a non-planar receiver resonator that is coupled to the rechargeable batteries of the VAD 750. Whether the patient is laying flat on the patient's back on the bed as shown in FIG. 8A or is lying on the patient's side as shown in FIG. 8B, the TETS 700 is still able to transfer a sufficient amount of energy to recharge the rechargeable batteries of the VAD 750. This feature of the TETS 700 according to embodiments of the present invention may not be possible in conventional systems that use only a single planar resonator for each of a transmitter and a receiver. In a conventional system, the planar resonators in the transmitter and the receiver may be oriented parallel to each other when the patient is laying flat on the patient's back on the bed as in FIG. 8A to effect energy transfer between the planar resonators. However, as the patient turns and lies on the patient's side as in FIG. 8B, the planar resonators of such a conventional system may then be oriented orthogonal to each other, which would result in zero or close to zero amount of energy being transferred. If the patient falls asleep and remains in this position for an extended period of time, the batteries of the VAD 750 may deplete completely to cause the VAD 750 of a conventional system to fail. This poses a risk to the patient if the VAD 750 losses power completely. Hence, by using a non-planar resonator in a TEST 700 in accordance with embodiments of the present invention, this risk to a patient can be minimized by enabling energy transfer in the system regardless of the orientation of the transmitter and receiver resonators relative to each other when the resonators are within an operating distance range of the TETS 700.

Referring back to FIG. 7A, although not shown, the TETS 700 may include any of the additional components and techniques described above to tune or detune the system to modulate the power delivered to the VAD 750 according to the needs and performance requirements of the patient. In an exemplary embodiment, the transmitter and receiver units 701 and 711 each include additional communications circuitry to establish a wireless communications channel between the receiver unit 701 and the transmitter unit 711 to communicate system information between the units. The system information can be used to adjust the tunable components of the system to modulate the power delivered to the receiver unit 801. The wireless communications channel can be a radio frequency signal or other wireless signal transmissions that are safe for the human body.

FIG. 7B illustrates a different embodiment of a TETS 760 in accordance with the present invention. In this embodiment, the rechargeable power storage device 716 is implanted near the back shoulder of a patient as shown. Because the receiver unit 711 is implanted near the back shoulder of a patient, the geometry of a planar resonator may be more suitable for implantation at that location than a non-planar resonator. As a result, instead of using a non-planar resonator in the receiver unit 711, the non-planar resonator is used in the transmitter unit 701 instead. Hence, in this embodiment, it is the transmitter unit 701 that has a non-planar transmitter resonator 762 to enable omni-orientation wireless energy transfer to a planar resonator 772 in the receiver unit 711. Because of the symmetry in the resonance coupling of the resonators, as long as at least one of the receiver or transmitter resonators is a non-planar resonator that spans a non-degenerate two-dimensional surface, power can be transmitted at a given operating distance regardless of one resonator's orientation relative to the other resonator. The operation of the TETS 760 is similar to those of the TETS 700 of FIG. 7A, and hence a description of the operation of the TETS 760 will not be repeated here.

The TETS in embodiments of the present invention can be advantageous in other scenarios as well. For example, a transmitter unit can be integrated into a wearable vest that a patient can wear, and the transmitter unit can be powered by a battery embedded in the vest. The patient can move around freely and go about the patient's daily activities while charging or powering an implanted VAD without requiring wires to connect the vest to the body and without the patient having to worry about the particular alignment of the vest to the body. A transmitter unit can be integrated into an office desk or other office furniture. As a patient moves around within the vicinity of the office desk or other office furniture at work, an implanted VAD can remain fully charged throughout the work day. A transmitter unit can also be integrated into an automobile such that a driver or a passenger with an implanted VAD can freely move around and adjust the person's sitting position within the automobile while charging an implanted VAD. Transmitter units can also be integrated into an airplane to allow a traveler to freely move around the cabin on long international flights while charging an implanted VAD.

Figure 9A:
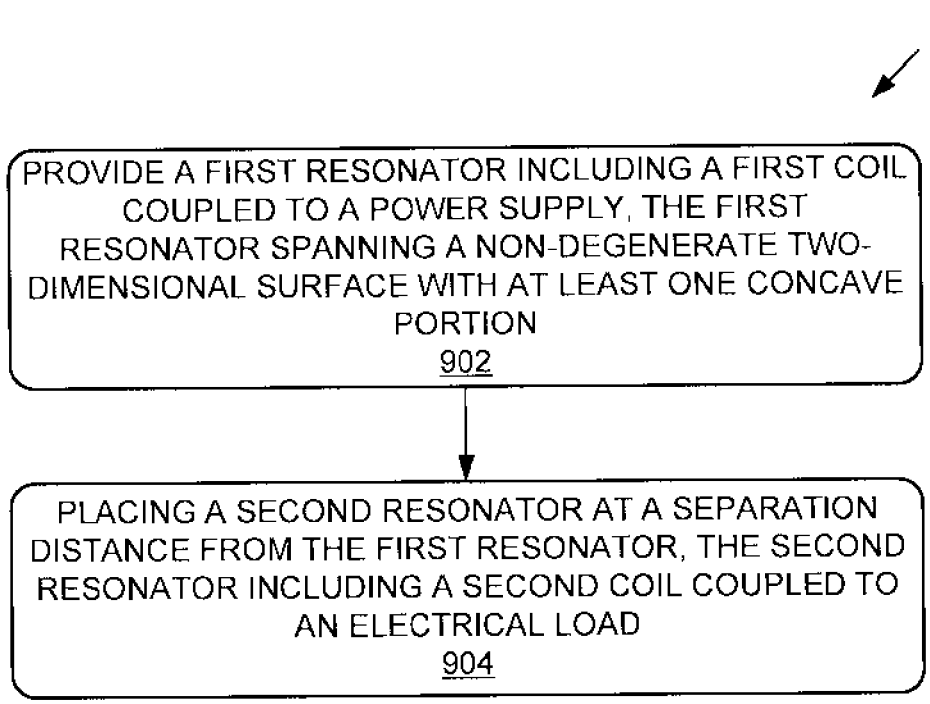
FIG. 9A illustrates an method for omni-orientational wireless energy according to one embodiment of the invention.

FIG. 9A shows a method for omni-orientational wireless energy transfer according to one embodiment of the present invention. At step 902, a transmitter resonator including a transmitter coil coupled to a power supply is provided. In this particular embodiment, the transmitter coil that is part of the transmitter resonator is a coil that spans a non-degenerate two-dimensional surface with at least one concave portion. When the power supply drives an electrical current through the transmitter coil, magnetic flux is generated around the transmitter resonator. At step 904, a receiver resonator is placed at a separation distance from the transmitter resonator. The receiver resonator includes a receiver coil that is coupled to an electrical load. When the separation distance is within an operating range, magnetic flux generated from the transmitter unit induces an electrical current to flow in the receiver coil of the receiver resonator. The electrical current flowing through the receiver coil can then be used to power the electrical load that is coupled to the receiver coil. Hence, power is transferred wirelessly from the transmitter resonator to the receiver resonator. By using a non-planar resonator that spans a surface area occupying three spatial dimensions in the transmitter resonator, magnetic flux is generated over a wider range of directions to enable a receiver resonator to intercept more of the generated magnetic flux in a wider range of spatial orientations relative to the transmitter resonator.

Figure 9B:
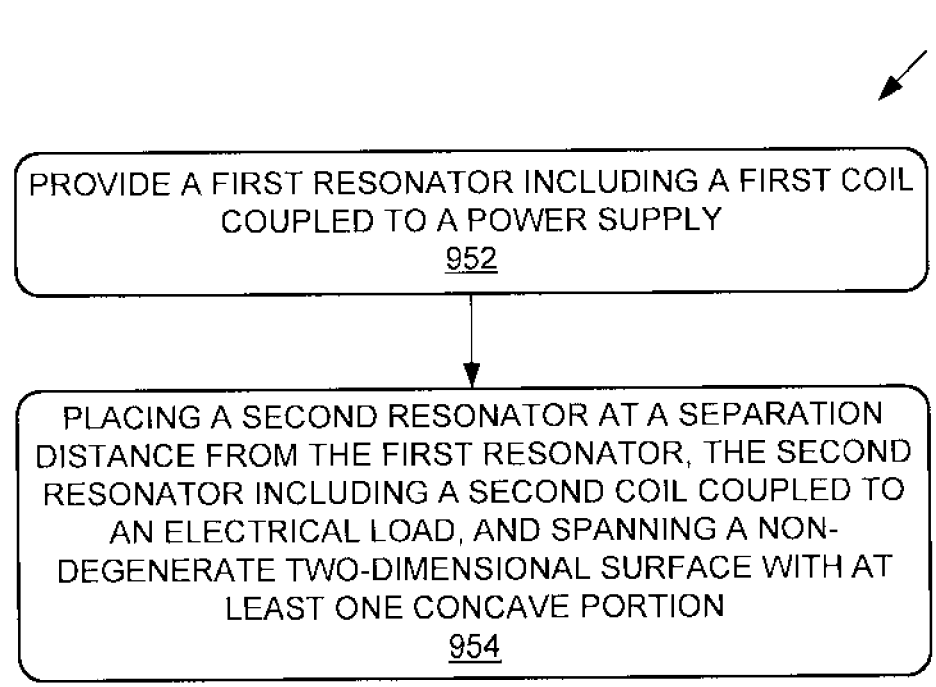
FIG. 9B illustrates an method for omni-orientational wireless energy according to another embodiment of the invention.

In a different embodiment, for example, the method 950 as shown in FIG. 9B, instead of the transmitter resonator, it is the receiver resonator that spans a non-degenerate two-dimensional surface with at least one concave portion. In both instances, the principles of the operations for omni-orientational wireless energy transfer are the same. When at least one of the resonators spans a non-degenerate two-dimensional surface such as those surfaces disclosed herein, energy can be transferred between the resonators regardless of the orientation of one resonator relative to the other resonator. While the flow diagrams in the figures show a particular order of operations performed by certain embodiments of the invention, it should be understood that such order is exemplary (e.g., alternative embodiments may perform the operations in a different order, combine certain operations, overlap certain operations, etc.).

Although some specific embodiments of the invention has been described in relation to a transcutaneous energy transfer system (TETS) to wirelessly transmit power to an implanted medical device through the skin of a patient, the advantages of using a non-planar resonator in a wireless energy transfer system can be applied to other applications as well. For instance, embodiments of the present invention can be used to power or recharge robots that are free to roam around a manufacturing facility, where the orientation of a receiver unit in the robots may vary relative to a stationary transmitter unit installed in the manufacturing facility. In general, embodiments of the present invention can be used in any application to wirelessly transfer energy between two objects, where at least one of the objects is free to move around such that the relative orientation of the two objects may change.

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

What is claimed is:

1. A system for wireless energy transfer comprising:
a transmitter unit including a first electromagnetic resonator having a first coil configured to wirelessly transmit power through a magnetic flux, wherein the first coil is rigidly shaped to form a first outline of a first surface; and
a receiver unit including a second electromagnetic resonator having a second coil configured to wirelessly receive power through the magnetic flux, wherein the second coil is rigidly shaped to form a second outline of a second surface;
wherein at least one of the first surface or the second surface is a non-planar surface occupying three spatial dimensions, and wherein the non-planar surface shapes the magnetic flux to wirelessly transfer power when the rigidly shaped first coil and second coil and physically decoupled and freely movable relative to each other.

2. The system of claim 1, wherein at least one electromagnetic resonator is freely movable relative to the other electromagnetic resonator when the at least one electromagnetic resonator is not spatially restricted by an external structure.

3. The system of claim 1, wherein the non-planar surface is a non-degenerate two-dimensional surface having one or more concave portions.

4. The system of claim 1, wherein a power transfer between the transmitter unit and the receiver unit is at least 25% of a maximum power transfer between the units in any relative orientation of the first electromagnetic resonator and the second electromagnetic resonator within an operating distance.

5. The system of claim 1, wherein one or more of the first coil or the second coil is a Litz wire coil that spirals along the non-planar surface to a rim of the non-planar surface.

6. The system of claim 1, wherein the transmitter unit is coupled to a power supply, wherein the receiver unit is coupled to a power storage device in one or more of an implantable medical device, a piece of wearable clothing, a wearable accessory, or a stationary object, and wherein the non-planar surface is configured to transfer the magnetic flux between the electromagnetic resonators such that the receiver unit intercepts the magnetic flux to induce an electrical current that meets a power requirement of the power storage device regardless of a relative orientation of the electromagnetic resonators within an operating distance.

7. The system of claim 1, wherein at least one of the electromagnetic resonators is coupled to a tunable capacitor or a network of capacitive elements to tune a resonant frequency of the system to maximize a voltage gain at the receiver unit.

8. The system of claim 1, wherein at least one of the electromagnetic resonators is coupled to a tunable resistor or a network of resistive elements to tune a quality factor "Q" of the system to maximize a voltage gain at the receiver unit.

9. The system of claim 1, wherein the receiver unit and the transmitter unit further comprise respective communications circuitry to establish a communications channel between the receiver unit and the transmitter unit to communicate system information used to modulate a power output of the transmitter unit.

10. A unit for use in an omni-orientational wireless energy transfer system to wirelessly transfer power through a shaped magnetic flux, the unit comprising:
an electromagnetic resonator having a first coil that is rigidly shaped to form a first outline of a non-planar surface occupying three spatial dimensions, wherein a shape of the non-planar surface is configured to transfer a magnetic flux with a rigidly shaped second coil of a second unit having a second electromagnetic resonator, and wherein the non-planar surface shapes the magnetic flux to wirelessly transfer power when the rigidly shaped first coil and second coil are physically decoupled and freely movable relative to each other.

11. The unit of claim 10, wherein the electromagnetic resonator is freely movable relative to the second electromagnetic resonator when at least one of the electromagnetic resonators is not spatially restricted by an external structure.

12. The unit of claim 10, wherein the non-planar surface is a non-degenerate two-dimensional surface having one or more concave portions.

13. The system of claim 10, wherein the first coil is a Litz wire coil that spirals along the non-planar surface to a rim of the non-planar surface.

14. The unit of claim 10, wherein the unit is coupled to a power storage device in one or more of an implantable medical device, a piece of wearable clothing, a wearable accessory, or a stationary object, and wherein the non-planar surface is configured to transfer the magnetic flux between the electromagnetic resonators such that the unit intercepts the magnetic flux to induce an electrical current that meets a power requirement of the power storage device regardless of a relative orientation of the electromagnetic resonators within an operating distance.

15. The unit of claim 10, wherein the electromagnetic resonator is coupled to a tunable capacitor or a network of capacitive elements to tune a resonant frequency of the system to maximize a voltage gain at one of the units.

16. The unit of claim 10, wherein the electromagnetic resonator is coupled to a tunable resistor or a network of resistive elements to tune a quality factor "Q" of the system to maximize a voltage gain at one of the units.

17. The unit of claim 10, wherein the units include respective communications circuitry to establish a communications channel between the units to communicate system information used to modulate a power output of one of the units.

18. A method for omni-orientational wireless energy transfer, the method comprising:

providing a first electromagnetic resonator including a first coil configured to wirelessly transmit power through a magnetic flux, wherein the first coil is rigidly shaped to form a first outline of a first surface; and placing a second electromagnetic resonator at an operating distance from the first electromagnetic resonator, the second electromagnetic resonator including a second coil configured to wirelessly receive power through the magnetic flux, wherein the second coil is rigidly shaped to form a second outline of a second surface;

wherein at least one of the first surface or the second surface is a non-planar surface occupying three spatial dimensions, and wherein the non-planar surface shapes the magnetic flux to wirelessly transfer power when the rigidly shaped first coil and second coil are physically decoupled and freely movable relative to each other.

19. The method of claim 18, further comprising establishing a communications channel between the first electromagnetic resonator and the second electromagnetic resonator to communicate information used to modulate a power output of the first electromagnetic resonator.

20. The method of claim 18, further comprising directing an output magnetic flux from the first electromagnetic resonator towards the second electromagnetic resonator with a flux concentrator.

* * * * *